United States Patent
Moore et al.

(10) Patent No.: US 6,803,217 B2
(45) Date of Patent: Oct. 12, 2004

(54) PROCESS FOR THE RECOVERY OF ORGANIC ACIDS

(75) Inventors: Kevin M. Moore, Mt. Zion, IL (US); Alexandra J. Sanborn, Lincoln, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 169 days.

(21) Appl. No.: 10/041,635

(22) Filed: Jan. 10, 2002

(65) Prior Publication Data

US 2002/0055155 A1 May 9, 2002

Related U.S. Application Data

(62) Division of application No. 09/631,638, filed on Aug. 2, 2000.
(60) Provisional application No. 60/147,031, filed on Aug. 3, 1999.

(51) Int. Cl.[7] .............................. C12P 7/62; C12P 7/40; C12P 7/56; C12P 7/50
(52) U.S. Cl. ....................... 435/135; 435/136; 435/139; 435/143
(58) Field of Search ................................ 435/135, 136, 435/139, 143; 562/580

(56) References Cited

U.S. PATENT DOCUMENTS

| | | | |
|---|---|---|---|
| 2,421,611 A | 6/1947 | Gray ............................ | 195/47 |
| 3,234,105 A | 2/1966 | Motizuki et al. ............. | 195/49 |
| 3,907,639 A | 9/1975 | Makover et al. .......... | 195/36 R |
| 3,912,592 A | 10/1975 | Makover et al. .......... | 195/31 R |
| 4,877,735 A | 10/1989 | Nogami et al. ............. | 435/138 |
| 4,882,277 A | 11/1989 | Czytko et al. .............. | 435/136 |
| 4,892,823 A | 1/1990 | Imai et al. .................. | 435/138 |
| 4,933,289 A | 6/1990 | Imai et al. ................ | 435/253.3 |
| 4,935,359 A | 6/1990 | Yin et al. .................... | 435/138 |
| 4,960,695 A | 10/1990 | Hoshino et al. .............. | 435/42 |
| 4,990,441 A | 2/1991 | Barthole et al. ............. | 435/138 |
| 5,002,881 A | 3/1991 | Van Nispen et al. ......... | 435/139 |
| 5,034,105 A | 7/1991 | Berglund et al. ........ | 204/182.4 |
| 5,312,741 A | 5/1994 | Hoshino et al. .............. | 435/42 |
| 5,391,770 A | 2/1995 | Le Fur et al. ............... | 549/315 |
| 5,503,750 A | 4/1996 | Russo, Jr. et al. .......... | 210/641 |
| 5,522,995 A | 6/1996 | Cockrem .................... | 210/637 |
| 5,681,728 A | 10/1997 | Miao .......................... | 435/136 |
| 5,705,373 A | 1/1998 | Yamaguchi et al. ........ | 435/138 |
| 5,834,231 A | 11/1998 | Stoddard et al. .............. | 435/42 |
| 5,852,211 A | 12/1998 | Dümpelmann et al. ..... | 562/580 |

FOREIGN PATENT DOCUMENTS

EP     0 174 624 A1    3/1986

OTHER PUBLICATIONS

EP 0 174 624 A1 (Boehm, W) Mar. 19, 1986 (abstract) World Patents Index [online]. London, U.K.: Derwent Publications, Ltd. [retrieved on Jan. 25, 2001]. Retrieved from: DialogClassic Web™, Accession No. 1986–077031/198612. International Search Report for PCT/US00/40538, (mailed Jan. 15, 2001).

Primary Examiner—David M. Naff
(74) Attorney, Agent, or Firm—Kirkpatrick & Lockhart LLP

(57) ABSTRACT

The present invention relates to a process for the recovery of an organic acid from a fermentation broth which comprises drying the fermentation broth to obtain a dried product, adding the dried product to a lower alcohol in the presence of an acid, and then removing the insoluble material to obtain an organic acid. In accordance with the recovery process of the present invention, organic acids of a high purity can be recovered in high yields from the whole fermentation solution containing various impurities with fewer steps as compared with conventional methods. In an embodiment, the fermentation broth is a whole broth containing insolubles including all microbial biomass present after fermentation. The insolubles are not separated until the organic acid is recovered. Prior to recovery, the organic acid may be esterified to the corresponding ester, and the insolubles are removed to recover the ester.

11 Claims, No Drawings

PROCESS FOR THE RECOVERY OF ORGANIC ACIDS

CROSS REFERENCE TO RELATED APPLICATION

This application is a Divisional of U.S. application Ser. No. 09/631,638, filed Aug. 2, 2000, which claims priority benefit of U.S. Provisional Application No. 60/147,031, filed Aug. 3, 1999, each of which is herein incorporated by reference in its entirety.

BACKGROUND OF THE INVENTION

1. Field of the Invention

The present invention relates to a process for the recovery and purification of organic acids from an aqueous solution, such as a fermentation broth.

2. Related Art

Organic acids are important chemicals of commerce, having many uses in the food and pharmaceutical industries. Lactic acid, for example, can be added to a variety of food stuffs as a preservative and is used in medical preparations and as a monomer in the manufacture of biodegradable plastics used in sutures, prosthetics and controlled release drug delivery systems.

Organic acids can be produced either by chemical synthesis or by microbial fermentation. Historically, organic acids were produced from animal fat or vegetable oil sources or from petroleum sources in substantially non-aqueous systems. However, since a number of microorganisms are known to produce valuable organic acids, methods have been developed for the recovery of organic acids produced by microbial fermentation. See, e.g., U.S. Pat. Nos. 5,681,728; 5,034,105; 5,002,881; and 4,882,277.

In the process for preparing organic acids, the step of fermentation is relatively simple. However, the steps of recovery and purification of the product, i.e. an organic acid, are usually complicated with poor efficiency. For example, recovery of a representative organic acid, 2-keto-L-gulonic acid, is made as follows.

2-keto-L-gulonic acid is a significant intermediate in the preparation of L-ascorbic acid (vitamin C), an essential nutrient. In the past, 2-keto-L-gulonic acid has been synthesized on an industrial scale using the Reichstein method (*Helvetica Chimica Acta* 17:311 (1934)). This method, however, has a number of disadvantages for commercial application, including the use of large quantities of solvents and the involvement of a number of complex reaction steps.

Accordingly, as an alternative to the Reichstein method, a number of processes employing one or more microorganisms have been developed for the commercial production of 2-keto-L-gulonic acid by fermentation. U.S. Pat. No. 2,421,611, for example, discloses a method involving microbial oxidation of D-glucose to 5-keto-D-gluconic acid, followed by chemical or microbial reduction to L-idonic acid and subsequent microbial oxidation to 2-keto-L-gulonic acid. Fermentative pathways involving oxidation of L-sorbose to 2-keto-L-gulonic acid via a sorbosone intermediate have also been developed using, for example, *Gluconobacter oxydans* (U.S. Pat. Nos. 4,935,359; 4,960,695; and 5,312,741), *Pseudogluconobacter saccharoketogenes* (U.S. Pat. No. 4,877,735), *Pseudomonas sorbosoxidans* (U.S. Pat. Nos. 4,892,823 and 4,933,289), and mixtures of microorganisms (U.S. Pat. Nos. 3,234,105; 3,907,639; and 3,912,592).

Similar to fermentation processes utilized for the manufacture of other organic acids, the 2-keto-L-gulonic acid which results as a metabolic product is usually neutralized by the addition of a base, e.g, sodium hydroxide or calcium hydroxide, in order to control the pH value and maintain favorable fermentation conditions. The product of the fermentation is an aqueous, biomass-containing fermentation solution in which the 2-keto-L-gulonic acid salt, e.g., the sodium, potassium, ammonium or calcium salt, is present in dissolved form. However, the free organic acids and their derivatives are the articles of commercial interest.

For example, in the industrial manufacture of L-ascorbic acid, the fermentatively produced 2-keto-L-gulonic acid must be transferred into an organic solvent, such as a lower alcohol. The salt form of 2-keto-L-gulonic acid, however, is practically insoluble in organic solvents. Therefore, for producing L-ascorbic acid with an industrial advantage, it is most preferable to employ the synthetic intermediate 2-keto-L-gulonic acid as a free acid.

Prior to conversion into ascorbic acid, however, 2-keto-L-gulonic acid must first be isolated from the fermentation broth. As described in U.S. Pat. No. 4,990,441, for example, 2-keto-L-gulonic acid can be recovered from a fermentation broth by a process comprising the steps of: (a) removing insoluble material from the broth by centrifugation in the presence of a flocculating agent, filtration in the presence of a flocculating agent and a filtration additive, or ultrafiltration; (b) removing inorganic cations by acidification; and (c) isolating 2-keto-L-gulonic acid by crystallization and drying. High yields of 2-keto-L-gulonic acid are difficult to obtain by this method, however, due to the number of steps required and the high solubility of 2-keto-L-gulonic acid in the crystallization mother liquor.

U.S. Pat. No. 5,852,211 describes a process for the conversion of the sodium salt of 2-keto-L-gulonic acid, which is present in an aqueous fermentation solution, into an alcoholic solution of the free acid. The disclosed process comprises the steps of: (a) crystallizing sodium 2-keto-L-gulonate monohydrate from an aqueous fermentation solution; (b) separating the sodium 2-keto-L-gulonate monohydrate crystals from the aqueous fermentation solution; (c) suspending the sodium 2-keto-L-gulonate monohydrate in a lower alcohol with acid at a pH in a range from about 1.5 to about 3.5 whereby the acid is converted to the insoluble sodium salt of the acid and the sodium 2-keto-L-gulonate monohydrate is converted to free 2-keto-L-gulonic acid; and (d) removing the sodium salt of the acid to obtain an alcoholic solution of 2-keto-L-gulonic acid. Due to the number of steps and the high solubility of the sodium 2-keto-L-gulonic acid that remains in the crystallization mother liquor, however, high yields of 2-keto-L-gulonic acid are likewise difficult to achieve.

Known methods for the recovery and purification of other organic acids produced by fermentation, such as lactic or succinic acid, also contain numerous steps and/or produce less than optimal yields. See, e.g., U.S. Pat. Nos. 5,681,728; 5,522,995; 5,503,750; and 5,034,105. Accordingly, there remains a need for a simplified process for the concentration, recovery and purification of organic acids from aqueous solutions, such as fermentation broths, in high yields.

SUMMARY OF THE INVENTION

It is therefore an object of the present invention to provide a simplified process for the recovery and purification of organic acids in high yields from a fermentation broth. Other objects, features and advantages of the present invention will be set forth in the detailed description of preferred embodiments that follows, and in part will be apparent from the description or can be learned by practice of the invention. These objects and advantages of the invention will be realized and attained by the methods particularly pointed out in the written description and claims hereof.

These and other objects are accomplished by the methods of the present invention, which, in a first embodiment, are broadly directed to a process for the recovery of an organic acid from a fermentation broth which comprises drying the fermentation broth to obtain a dried product, adding the dried fermentation product to a lower alcohol in the presence of an acid, and then removing the insoluble material to obtain the organic acid. Other preferred embodiments of the present invention will be described in more detail below.

It is to be understood that both the foregoing general description and the following detailed description are exemplary and explanatory only and are intended to provide further explanation of the invention as claimed.

DETAILED DESCRIPTION OF THE PREFERRED EMBODIMENTS

In one aspect of the invention there is provided a process for the recovery of an organic acid from a fermentation broth which comprises:

(a) drying the fermentation broth to obtain a dried product;

(b) adding the dried product to a lower alcohol in the presence of an acid; and (c) removing the insolubles to obtain an organic acid.

As used herein, the term "organic acid" or grammatical equivalents means a substituted or unsubstituted alkyl group containing one or more carboxyl groups, —COOH, i.e. a carboxyl acid. The organic acids can be obtained from a fermentation conversion of saccharides such as starch, sucrose or glucose or from n-paraffins.

A non-exclusive list of examples of organic acids which can be recovered using the inventive process includes lactic acid, 2-keto-L-gulonic acid, tartaric acid, citric acid, acetic acid, maleic acid, malic acid, malonic acid, succinic acid, salicylic acid, glycolic acid, glutaric acid, gluconic acid, benzoic acid, formic acid, propionic acid, pivalic acid, oxalic acid, toluic acid, stearic acid, ascorbic acid, pamoic acid, glutamic acid, fumaric acid or mixtures thereof. In a preferred embodiment, the recovered organic acid is lactic acid, 2-keto-L-gulonic acid, citric acid or gluconic acid.

It has been surprisingly and advantageously found that organic acids of a high purity can be recovered at high yields using the whole dried fermentation broth as the starting material. With the aid of the process in accordance with the invention, organic acids such as lactic acid and 2-keto-L-gulonic acid, which usually occur as a dissolved salt in the aqueous fermentation solution, can be recovered in a relatively simple and economical manner into an alcoholic solution of the free acid.

Following recovery of the organic acids according to the present invention, the organic acids can be further treated, if necessary, in order to render them suitable for their intended purpose. For example, the thus-obtained solution of 2-keto-L-gulonic acid can subsequently be converted into ascorbic acid in any known manner. See, e.g., U.S. Pat. No. 5,391,770.

Any fermentation broth containing the desired organic acid(s), a precursor thereof or its water-soluble salt can be used in the present invention. Such a fermentation broth, which is effected prior to the actual process in accordance with the invention, can be obtained by any conventional means, such as microbial fermentation. See, e.g., U.S. Pat. Nos. 5,834,231 and 5,705,373. Further, the microbes used in the fermentation process may be Protists (yeast or fungi) or bacteria, and the fermentation itself may be either aerobic or anaerobic.

The fermentation broth used in the present invention is typically, but not always, a fermentation broth produced by the cultivation of one or more microorganisms that produce a specific organic acid(s) and/or a precursor thereof. Any microorganism(s) which produces the desired organic acid can be used to prepare the fermentation broth. The organic acid producing microorganisms which can be used, for example, include bacteria belonging to the genera Lactobacillus, Pseudogluconobacter, Pseudomonas, Corynebacterium Acetobacter, Gluconobacter, Aspergillus, Brevibacterium and bacteria belonging to the genus Erwinia. See, e.g., Atkinson and Mavituna, *Biological Engineering and Biotechnology Handbook* 421 (1983).

A temperature suitable for each species of microorganism used is employed as the fermentation temperature. It is usually from about 25° C. to about 60° C. In addition, most of the organic acid-producing microorganisms have an acid sensitivity which require the medium to have a pH from about 3 to about 9.

The composition of the fermentation medium where an organic acid is produced using the above-mentioned microorganisms can be any one which is suitable for an organic acid producing microorganism to be used. In addition to water and an insoluble biomass, these fermentation broths generally contain the nutrients required by the microorganism(s) being employed to produce the organic acid. These nutrients include, but are not limited to, amino acids, inorganic and/or organic salts, carbohydrates, and various vitamins and growth factors.

In one preferred embodiment of the invention, at least part of the insolubles are first removed from the fermentation broth prior to the drying step of the inventive process. The insolubles, e.g., microorganisms which form the biomass and salts, are preferably removed at the end of fermentation and can be removed by any known mechanical separation technique. Such techniques include, but are not limited to, filtration, e.g., ultrafiltration and microfiltration, and separation, e.g., centrifugation and decanting, by which, on the whole, only undissolved and/or relatively high molecular weight substances are removed. In a preferred embodiment, at least part of the insolubles are removed from the fermentation broth by filtration prior to the drying step. Most preferably, at least part of the insolubles are removed by ultrafiltration.

In another preferred embodiment, at least about 90% of the insolubles are first removed from the fermentation broth prior to the drying step. The fermentation broth from which some or all of the insolubles have been removed can then be concentrated prior to drying. In one embodiment, the process for concentrating the fermentation broth is by evaporation.

Therefore, in one embodiment of the invention, the whole fermentation broth can be used as the starting material for the recovery of the organic acid. In another embodiment, some or all of the insoluble material can be removed from the fermentation broth prior to the drying step of the inventive process. It is understood that a complete or partial removal of the insolubles prior to the drying is not necessary for the purpose of carrying out the inventive process.

In the inventive process, the fermentation broth is dried to obtain a dried product. The fermentation broth can be dried by any known process, e.g., by means of a spray dryer, a spin flash dryer or a fluidized bed dryer. In a preferred embodiment, the fermentation broth is dried by the use of a spray dryer. In another preferred embodiment, the moisture percentage of the dried product is from about 0.1% to about 20% moisture, more preferably from about 0.1% to about 10%. The dried product which is obtained contains, among other substances, the desired organic acid and all or part or none of the biomass. It was surprising and particularly advantageous that the fermentation broth could be dried, e.g., spray dried, to obtain an easily handled free flowing powder.

According to the inventive process, the dried fermentation broth containing, inter alia, the desired organic acid, a precursor thereof or its salt, is added to a lower alcohol in the presence of an acid. In a preferred embodiment, the concentration of the organic acid added to the lower alcohol is from about 50 g/L to about 100 g/L. The lower alcohol employed in the inventive process can be any lower alcohol which allows for the selective recovery of the desired organic acid. Suitable lower alcohols can be determined empirically by those skilled in the art and include, e.g., methanol, ethanol, propanol, butanol and glycol. In a preferred embodiment, the lower alcohol is methanol or ethanol, more preferably anhydrous methanol or ethanol.

In general, the amount of lower alcohol and acid employed in the inventive process can be any amount which allows for the selective recovery of the desired organic acid. In addition, the amount of acid added will be proportional to the amount of dried product. In a preferred embodiment, the acid is added in stoichiometric proportions or in excess, preferably about 1.2 equivalents of acid is added.

The acid can be any acid which allows for the selective recovery of the desired organic acid. For example, a strong acid of low water content can be used in the inventive process. The water content of the acid is not critical for the process. However, the concentration of water in the resulting organic acid/alcohol solution determines the equilibrium conversion of a subsequent esterification. Therefore, from an industrial-economical point of view, acids of low water content, i.e., acids more appropriately denoted as "concentrated," are preferably used. In a preferred embodiment, the water content of the acid is about 15% or less. Examples of such acids are sulphuric acid, nitric acid, hydrochloric acid, hydrobromic acid and phosphoric acid, and even gaseous hydrogen chloride. In a preferred embodiment, concentrated sulphuric acid or hydrochloric acid is used. More preferably, concentrated sulfuric acid is used.

In one embodiment of the invention, the dried fermentation product can first be suspended in the lower alcohol prior to the addition of the acid. The desired organic acid can also be obtained in another embodiment of the invention whereby the dried product is added together with the acid to a lower alcohol. It is therefore understood that both the simultaneous and subsequent addition of acid are included within the scope of the inventive process, although the subsequent addition of acid is preferred.

Preferably, the temperature at which the dehydration and acid reactions are carried out lies in the range from about 25° C. to about 60° C. In addition, the resulting organic acid should be soluble in the reaction mixture.

In another embodiment of the invention, there is provided a process for the recovery of an organic acid ester from a fermentation broth. Carboxylic acids react with alcohols in the presence of a strong acid, such as sulfuric acid, to produce esters. Under certain conditions the obtained free organic acid of the present invention, together with a lower alcohol in the presence of an acid, can be converted into its corresponding organic acid lower alkyl ester. Accordingly, it is understood that the recovered free organic acid as well as the corresponding organic acid ester are included within the scope of the inventive process.

According to the inventive process, the insolubles are subsequently removed from the solution to obtain the desired organic acid. After the dried product is added to a lower alcohol in the presence of an acid, insoluble salts, e.g., $Na_2SO_4$, $CaSO_4$, $K_2SO_4$, $(NH_4)_2SO_4$, can be removed readily from the reaction mixture. The removal of the insoluble salts, as well as other insoluble substances, e.g., residues of biomass or proteins, can be carried out by any known process, such as filtration and/or centrifugation. In a preferred embodiment, the insolubles are removed by filtration. The resulting alcoholic filtrate containing the desired organic acid has a very high purity.

Therefore, in accordance with the recovery process of the present invention, organic acids of a high purity, i.e., greater than about 80%, can be recovered in high yields, i.e., greater than about 90%, preferably 95% to 99%, from the whole fermentation solution containing various impurities with fewer steps as compared with conventional methods. The disadvantages of prior art processes, such as the complete removal of biomass and proteins, the use of cation exchangers to remove metal ions from the aqueous fermentation solutions as well as the crystallization of the organic acid, are thereby avoided.

All patents and publications cited in this disclosure are indicative of the level of skill of those skilled in the art to which this invention pertains and are all herein incorporated by reference in their entirety.

Having now generally described the invention, the same will be more readily understood through reference to the following Examples which are provided by way of illustration, and are not intended to be limiting of the present invention, unless specified.

EXAMPLE 1

A fermentation broth was prepared as described in U.S. Pat. No. 5,834,231 containing 84 g/L 2-keto-L-gulonic acid, 4 g/L sorbose and 136 g/L total dry solids and spray-dried on a high pressure nozzle sprayer (APV Americas; Tonawanda, N.Y.). The feed was preheated to 170° F., and dried with a 495° F. inlet and a 198° F. outlet temperature. A total of 8 gallons of feed was dried to give 10.2 lbs. of dried product at 8% moisture.

25 g of the spray dried product was slurried into 250 ml of anhydrous methanol. 3.2 ml of sulfuric acid was added to the solution over 20 minutes while stirring. The slurry was stirred for an additional 60 minutes, filtered and the solids washed with 150 ml of additional methanol. The product filtrate of 320 ml contained 35 g/L 2-keto-L-gulonic acid and 1.7 g/L of 2-keto-L-gulonic acid methyl ester. The cake of 12 grams contained 3.8% 2-keto-L-gulonic acid and 0.4% 2-keto-L-gulonic acid methyl ester, for a yield of 96%.

EXAMPLE 2

A fermentation broth made similar to that in Example 1 was first ultrafiltered using a 100,000 molecular weight cutoff membrane to remove cell solids, and then evaporated to a 1.2 g/ml density before spray drying. The feed was preheated to 165° F., and dried with a 495° F. inlet and 200° F. outlet temperature. Feed dry solids was 39.2 wt %. A total of 10 gallons of feed was dried, to give 42 lbs. of dry product at 15% moisture.

36 g of the spray dried product was slurried into 250 ml of anhydrous methanol. 4.2 ml of concentrated sulfuric acid was added over 20 minutes. The slurry was stirred for an additional 60 minutes, filtered, and washed with 150 ml of methanol. The product filtrate of 335 ml contained 67 g/L 2-keto-L-gulonic acid and 1 g/L 2-keto-L-gulonic acid methyl ester. The cake of 31 g contained 3.0% 2-keto-L-gulonic acid with no methyl ester, for a yield of 96%.

EXAMPLE 3

10 ml of product filtrate obtained by the procedure of Example 2, but containing 71.9 g/L of 2-keto-L-gulonic acid, was placed in a test tube. To this solution was added 0.14 ml of concentrated sulfuric acid. The test tube was placed in an oven at 60° C. for 1 hour to give 1.5g/L of 2-keto-L-gulonic acid and 77.1 g/L of methyl ester.

EXAMPLE 4

A fermentation broth of calcium lactate, made from the fermentation of *Lactobacillus casei* on dextrose, was ultra-filtered and spray dried, using the procedures of Examples 1 and 2, to obtain a dry product containing 70.3 wt % lactic acid. 25 g of the spray dried calcium lactate was slurried into 500 ml anhydrous ethanol. 6.4 ml of concentrated sulfuric acid was added over 30 minutes. The slurry was stirred for an additional 60 minutes, filtered, and washed two times with 100 ml ethanol. The filtrate of 490 ml contained 59.1 g/L lactic acid and the wash of 195 ml contained 20.1 g/L lactic acid. The cake of 25 g contained 1.8 g/kg lactic acid for a yield of 99%.

EXAMPLE 5

17.5 g of the spray dried calcium lactate was slurried into 125 ml of anhydrous ethanol. 4.9 ml of concentrated sulfuric acid was added over 30 minutes. The slurry was allowed to heat to 75° C. with stirring for one hour. The slurry was filtered and washed two times with 100 ml of ethanol. The filtrate of 200 ml contained 67.9 g/L ethyl lactate and 1.6 g/L lactic acid for a total yield of 86.6%.

In view of the foregoing description taken with the Examples, those skilled in the art will be able to practice the invention in various enablements and embodiments without departing from the spirit and scope of the invention as defined in the appended claims.

What is claimed is:

1. A process for the recovery of an organic acid ester from a fermentation broth comprising:

(a) conducting a fermentation with an organic acid producing microorganism to produce a fermentation broth containing an organic acid and insolubles comprising all microbial biomass resulting from said fermentation;

(b) drying said fermentation broth to obtain a dried product containing said organic acid and said insolubles comprising said mircobial biomass, wherein said drying occurs without prior removal of any of said insolubles comprising said microbial biomass from said fermentation broth;

(c) adding said dried product from step (b) to a lower alcohol in the presence of a strong acid to obtain a free organic acid in a solution containing said insolubles, (d) esterifying the free organic acid to the corresponding organic acid ester in a solution containing said insolubles; and (e) removing said insolubles comprising said microbial biomass to obtain a solution comprising said organic acid ester.

2. The process of claim 1, wherein in step (c) the concentration of said organic acid added to said lower alcohol is from about 50 g/L to about 100 g/L.

3. The process of claim 1, wherein in step (b) drying comprises spray drying said fermentation broth.

4. The process of claim 1, wherein the temperature in steps (c) and (d) is from about 25° C. to about 6° C.

5. The process of claim 1, wherein in step (c) said lower alcohol is selected from the group consisting of methanol, ethanol, propanol, butanol and glycol.

6. The process of claim 1, wherein in step (c) about 1.2 equivalents of strong acid is present.

7. The process of claim 1, wherein in step (c) said strong acid is selected from the group consisting of sulphuric acid, hydrobromic acid, hydrochloric acid and phosphoric acid.

8. The process of claim 7, wherein in step (c) said acid is sulphuric acid.

9. The process of claim 1, wherein in step (e) the process for removing insolubles comprises filtration.

10. The process of claim 1, wherein said organic acid comprises lactic acid, 2-keto-L-gulonic acid, citric acid or gluconic acid.

11. The process of claim 10, wherein said organic acid is 2-keto-L-gulonic acid.

* * * * *

UNITED STATES PATENT AND TRADEMARK OFFICE
CERTIFICATE OF CORRECTION

PATENT NO. : 6,803,217 B2
DATED : October 12, 2004
INVENTOR(S) : Kevin M. Moore et al.

It is certified that error appears in the above-identified patent and that said Letters Patent is hereby corrected as shown below:

Column 8,
Line 28, delete "6° C. " and substitute therefore -- 60° C. --

Signed and Sealed this

Twenty-fourth Day of May, 2005

JON W. DUDAS
*Director of the United States Patent and Trademark Office*